United States Patent
Dedroog et al.

(10) Patent No.: US 10,478,074 B1
(45) Date of Patent: Nov. 19, 2019

(54) METHOD FOR DETERMINING PATIENT SUITABILITY FOR A SURGICAL PROCEDURE

(71) Applicant: Dextera AS, Oslo (NO)

(72) Inventors: Frank Dedroog, Barcelona (ES); Javier Murillo-Castarlenas, Saragossa (ES); Pilar Garcia-Navarro, Saragossa (ES); Adrian Navas-Montilla, Saragossa (ES); Jose Ramirez-Rodriguez, Saragossa (ES)

( * ) Notice: Subject to any disclaimer, the term of this patent is extended or adjusted under 35 U.S.C. 154(b) by 0 days.

(21) Appl. No.: 16/186,965

(22) Filed: Nov. 12, 2018

Related U.S. Application Data

(63) Continuation-in-part of application No. 16/016,196, filed on Jun. 22, 2018.

(60) Provisional application No. 62/747,274, filed on Oct. 18, 2018.

(51) Int. Cl.

| | | |
|---|---|---|
| *A61B 5/02* | (2006.01) | |
| *A61B 5/0205* | (2006.01) | |
| *A61B 5/145* | (2006.01) | |
| *G16H 50/50* | (2018.01) | |
| *A61B 5/08* | (2006.01) | |
| *A61B 5/021* | (2006.01) | |
| *A61B 5/024* | (2006.01) | |

(52) U.S. Cl.
CPC ........ *A61B 5/02028* (2013.01); *A61B 5/0205* (2013.01); *A61B 5/14542* (2013.01); *G16H 50/50* (2018.01); *A61B 5/021* (2013.01); *A61B 5/024* (2013.01); *A61B 5/0816* (2013.01)

(58) Field of Classification Search
None
See application file for complete search history.

(56) References Cited

U.S. PATENT DOCUMENTS

| | | | |
|---|---|---|---|
| 7,311,680 B2 * | 12/2007 | Lenhart | A61H 31/00 601/41 |
| 9,226,672 B2 | 1/2016 | Taylor | |
| 2007/0014452 A1 * | 1/2007 | Suresh | G06F 19/3481 382/128 |

* cited by examiner

*Primary Examiner* — Brian T Gedeon
(74) *Attorney, Agent, or Firm* — r.r (princeton); Roy Rosser

(57) ABSTRACT

A system and method for determining a patient's suitability for a proposed surgical procedure is disclosed in which a simulated, procedure specific hemodynamic profile of an individual patient is obtained using a hemodynamic simulation module operating on a digital processor using a patient specific hemodynamic calculation parameter set. This is used by a trained clinician to evaluate whether the patient is a suitable candidate to undergo the proposed surgery. The patient specific hemodynamic calculation parameter set is obtained by optimizing a generic hemodynamic calculation parameter set. Optimization is done automatically by adjusting the generic hemodynamic calculation parameter set based on the comparison of simulated profiles corresponding to measured hemodynamic profiles of the patient in a non-operation situation. The automatic adjustment is guided by a Damped Least Squares Method and related algorithms.

11 Claims, 5 Drawing Sheets

METHOD FOR DETERMINING PATIENT SUITABILITY FOR A SURGICAL PROCEDURE

CROSS-REFERENCE TO RELATED APPLICATIONS

This application is a continuation-in-part application of U.S. patent application Ser. No. 16/016,196 filed on Jun. 22, 2018, entitled "Method and Apparatus For Full-System, Cardiovascular Simulation and Prediction", and claims priority to U.S. Ser. No. 62/747,274 filed Oct. 18, 2018, entitled "Introduction to lumped hemodynamic models", as well as to U.S. Provisional Patent Application Ser. No. 62/688,686 filed Jun. 22, 2018 entitled "Simplified Closed Loop Cardio Simulator", U.S. Provisional Patent Application Ser. No. 62/577,466 filed Oct. 26, 2017 entitled "Closed Loop Cardio Simulator", U.S. Provisional Patent Application Ser. No. 62/530,898 filed Jul. 11, 2017 entitled "Exact Energy Balance Solver", U.S. Provisional Patent Application Ser. No. 62/523,445 filed Jun. 22, 2017 entitled "Global Multiscale Human Circulation Simulator", the contents of all of which are fully incorporated herein by reference.

BACKGROUND OF THE INVENTION

(1) Field of the Invention

The invention relates to methods and apparatus for determining patient suitability for procedures, and more particularly, to using hemodynamic simulation modules, operable on digital processors, to provide simulated, procedure specific, whole-body, hemodynamic profiles of individual patients as aids in determining a patient's suitability for proposed interventions, including surgical interventions.

(2) Description of the Related Art

The technical problem of predicting the consequences of patient interventions, particularly surgical interventions, and, therefore, whether or not a particular patient is a suitable candidate for a particular procedure, is inherent in the technical fields of medicine and surgery. It would, for instance, be of considerable use for a surgeon, or other trained clinician, to be able to accurately predict the actual consequences of an intended action before the action is taken. An example of where such a capability would be of considerable benefit is in predicting whether or not a patient is fit enough to undergo laparoscopic surgery.

Laparoscopic surgery, also called minimally invasive surgery, is a surgical technique in which operations are performed through small incisions that are typically 0.5-1.5 cm long. Specialized surgical instruments, such as graspers, scissors and clip appliers, all of which are only 5-10 mm in diameter, are typically introduced by the surgeon into the patient though such an incision. The most important of these is the laparoscope, a long fiber optical cable system that typically allows both viewing and illumination of the region under surgery.

Laparoscopic surgery offers many benefits, such as, but not limited to, less pain, shorter recovery times, and reduced exposure of internal organs to possible infection. However, there are also disadvantages, including that the surgeon having limited visibility, poor depth perception and a limited range of motion. To ameliorate some of the difficulties, laparoscopic surgery is typically performed with the patient in a head-down, or Trendelenburg, position, and with carbon dioxide insufflation of the abdominal cavity. While maximizing the surgeon's visual field, and facilitating instrumentation, these surgery specific situations that the patent is placed in may result in serious complications, especially if they are to be endured for any great length of time. In particular, the head-down positioning, and abdominal cavity insufflation, may have adverse hemodynamic effects such as, but not limited to, increased blood pressure and reduced cardiac output. It would, therefore, be beneficial for a surgeon to able to predict whether or not a patient is in sufficiently good health to endure the rigors of laparoscopic surgery. A system and method of predicting, or simulating, the hemodynamic consequences of placing a particular patient in such a surgical situation would, therefore, be of considerable use.

While mathematically based, cardio-vascular simulation and prediction systems exist, the relevant prior art often focuses on specific regions of the overall human hemodynamic system as in, for instance, U.S. Pat. No. 9,226,672 issued to Taylor on Jan. 5, 2016 entitled "Method and system for patient-specific modeling of blood flow" that describes a system for determining cardiovascular information for a patient.

This patent discloses a computer system configured to receive patient-specific data regarding a geometry of the patient's heart, and create a three-dimensional model representing at least a portion of the patient's heart based on the patient-specific data. The disclosed system may also be configured to create a physics-based model relating to a blood flow characteristic of the patient's heart and determine a fractional flow reserve within the patient's heart based on the three-dimensional model and the physics-based model.

The human hemodynamic system is complex and includes many compensatory mechanisms, such as, but not limited to, the negative feedback loop of the baroreflex, that may interact with any interventions, be they surgical, medicinal or merely mechanical such as, but not limited to, a change in patient orientation, or applied pressure to an organ.

A full-system, closed loop cardiovascular simulation and prediction system may, therefore, be a requirement for meaningfully accurate prediction.

Furthermore, the simulation is preferably tailored to be as accurate a model of a specific individual. Such a system may provide hemodynamic values that may accurately reflect the complex interactions of the whole human system of a specific patient in a specific, surgical situation.

Various implementations are known in the art, but fail to address all of the problems solved by the invention described herein. Various embodiments of this invention are illustrated in the accompanying drawings and will be described in more detail herein below.

BRIEF SUMMARY OF THE INVENTION

An inventive system and method for determining a patient's suitability for a proposed procedure such as, but not limited to, a surgical procedure, is disclosed.

In a preferred embodiment, a simulated hemodynamic profile of an individual patient that is procedure specific, i.e., indicative of how that specific patient's cardio-vascular system will perform under the conditions necessary for that procedure, may be obtained using a hemodynamic simulation module operating on a digital processor. This may, for instance, be accomplished by first obtaining a patient specific hemodynamic calculation parameter set. This may then be used by a hemodynamic simulation module having a mathematical hemodynamic model representative of the patient's entire cardio-vascular system, i.e., a full-system, closed loop model. The simulated, procedure specific, hemodynamic profile of the patient may then be used by the surgeon, or other trained clinician, to evaluate whether or not the patient is a suitable candidate to undergo the proposed surgery.

The patient specific hemodynamic calculation parameter set may, for instance, be obtained by starting with a generic hemodynamic calculation parameter set. The generic hemodynamic calculation parameter set may, for instance, be a set of parameters needed to populate the mathematical hemodynamic module being used for the simulation. These parameters may be obtained from data representative of a population having one, or more, observable characteristics in common with the patient. These observable characteristics may, for instance, be demographic features such as, but not limited to, age, gender, or ethnicity; or measurable observables such as, but not limited to, weight, or height; or historical attributes such as, but not limited to, diet, or a history regarding prior surgeries, alcohol consumption, smoking, drug use, medication use, or some combination thereof.

The generic hemodynamic calculation parameter set may then be adjusted so that the hemodynamic simulation module may provide accurate simulations of the specific individual being evaluated. The adjustments to the calculation parameters may, for instance, be such that they provide an accurate simulation of an already measured hemodynamic response of the patient.

The already measured hemodynamic response may be a measured, first situation, hemodynamic profile. This measured, first situation, hemodynamic profile may, for instance, consist of measurable parameters such as, but not limited to, one or more arterial circulation parameters, such as, but not limited to, a systolic and a diastolic arterial blood pressures; one or more cardiac parameters, such as, but not limited to, a heart rate, a systolic and a diastolic, right and left, ventricular pressures; and one or more respiration parameters, such as, but not limited to, an arterial and a venous oxygen saturation, or some combination thereof. These measurable parameters may be measured on a particular patient while they are positioned in a particular, first, situation, such as, but not limited to, sitting on a chair in a temperature controlled room.

The adjustment of the generic hemodynamic calculation parameter set to obtain the patient specific hemodynamic calculation parameter set may be done by a trained physician, or it may be done automatically by an optimization module operative on a digital processor, or a combination thereof. The automated optimization may, for instance, utilize an iterative optimization algorithm such as, but not limited to, a Damped Least Squares Method.

The patient specific hemodynamic calculation parameter set may be deemed to have been found when the simulated, hemodynamic profile of the patient, using the adjusted, hemodynamic calculation parameter set, agrees to sufficient accuracy with the measured, hemodynamic profile of that patient situated in the same situation. The adjusted, hemodynamic calculation parameter set that produces that agreement may, for instance, become the patient specific hemodynamic calculation parameter set.

This patient specific hemodynamic calculation parameter set may then be used by the hemodynamic simulation module to automatically calculate a further simulated, hemodynamic profile, that may now be a simulated, procedure specific, hemodynamic profile. This simulated, procedure specific, hemodynamic profile may predict how the patient's cardio-vascular system would perform if the patient were to undergo the proposed surgical procedure. This simulated, procedure specific, hemodynamic profile may, therefore, be used by a trained clinician to determine if the patient is a suitable candidate to undergo the proposed surgery.

The hemodynamic simulation module may use a suitably constructed mathematical hemodynamic model that may, for instance, be a lumped circuit, mathematical model, as described in more detail below. Such a model may be representative of the cardio-vascular circulation of the entire body of a human.

Therefore, the present invention succeeds in conferring the following, and others not mentioned, desirable and useful benefits and objectives.

It is an object of the present invention to provide an accurate simulation of a specific patient's cardio-vascular response to undergoing a proposed surgical procedure.

DETAILED DESCRIPTION OF THE INVENTION

Figure 1:
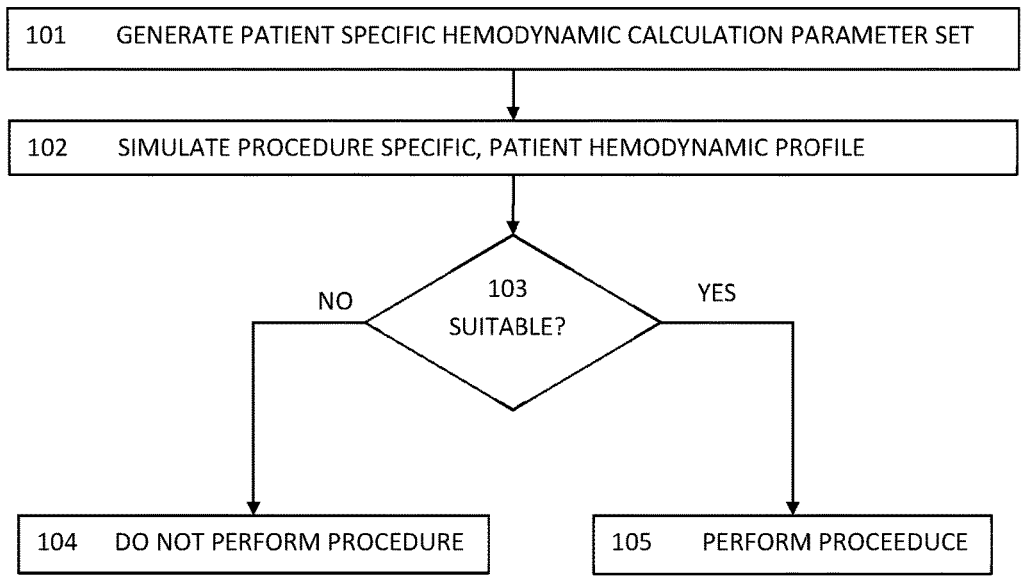
FIG. 1 is a schematic flow diagram showing representative steps for determining a patient's suitability for a proposed surgical procedure of one embodiment of the present invention.

The preferred embodiments of the present invention will now be described in more detail with reference to the drawings in which identical elements in the various figures are, as far as possible, identified with the same reference numerals. These embodiments are provided by way of explanation of the present invention, which is not, however, intended to be limited thereto. Those of ordinary skill in the art may appreciate upon reading the present specification and viewing the present drawings that various modifications and variations may be made thereto without departing from the spirit of the invention.

FIG. 1 is a schematic flow diagram showing representative steps for determining a patient's suitability for a proposed surgical procedure of one embodiment of the present invention.

In Step 101, "GENERATE PATIENT SPECIFIC HEMODYNAMIC CALCULATION PARAMETER SET", parameters to be used in a hemodynamic simulation module may be obtained that are representative of a specific individual. The patient specific hemodynamic calculation parameter set may, for instance, be a set of values needed to populate a mathematical model such as, but not limited to, a lumped circuit model representative of a human cardio-vascular circulation system in its entity, as described in detail below.

In Step 102, "SIMULATE PROCEDURE SPECIFIC, PATIENT HEMODYNAMIC PROFILE", the patient specific hemodynamic calculation parameter set may be used by the hemodynamic simulation module to calculate a simulated hemodynamic profile indicative of how the patient may respond to being in a situation required by a specific surgical procedure. For meaningful simulation, a full-system, closed loop hemodynamic model representative of the entity of the human body may be used in the simulation module. The profile may, for instance, include simulated parameters such as, but not limited to, a systolic and a diastolic arterial blood pressures, one or more cardiac parameters such as, but not limited to, a heart rate, a systolic and a diastolic, right and left, ventricular pressure; and one or more respiration parameters, such as, but not limited to, an arterial and a venous oxygen saturation; or some combination thereof. The surgical procedure specific situation may, for instance, be that required by a particular type of laparoscopic surgery, such as, but not limited to, the patient being in a head-down situation while having their abdominal cavity insufflated with carbon dioxide.

In Step 103 "SUITABLE?", a suitably trained and knowledgeable clinician may examine the simulated, procedure specific, hemodynamic profile for the patient, and based on the values presented, may make a determination as to whether not the patient is a suitable candidate for the proposed procedure. This determination may also, or instead, be made, or aided by, a set of predetermined threshold values of one or more or the values of the hemodynamic profile.

If the decision is "No", i.e., the patient may be deemed not to be in physically fit enough to undergo the proposed surgical procedure, then the determination may proceed to Step 104 "DO NOT PERFORM PROCEDURE", in which the clinician may decide not to do the procedure, and to either alter the procedure, or decide on a different course of treatment, or intervention.

If the decision is "Yes", i.e., the patient may be deemed physically fit enough to undergo the proposed surgical procedure, then the determination may proceed to Step 105 "PERFORM PROCEDURE", and the procedure may be undertaken with the assurance that the patient is predicated to survive it.

Figure 2:
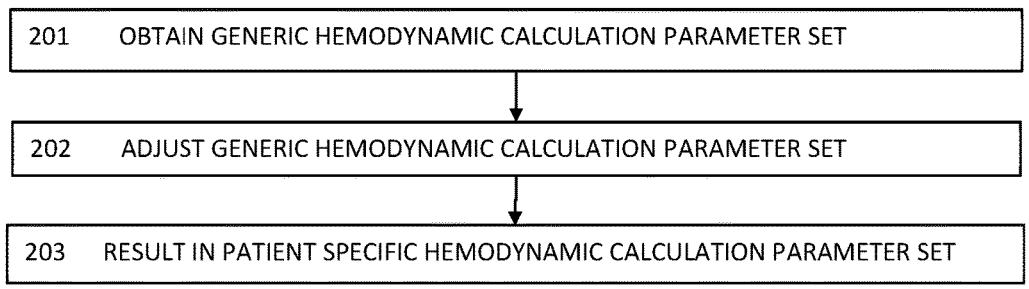
FIG. 2 is a schematic flow diagram showing representative steps for obtaining a patient specific hemodynamic calculation parameter set of one embodiment of the present invention.

FIG. 2 is a schematic flow diagram showing representative steps for obtaining a patient specific hemodynamic calculation parameter set of one embodiment of the present invention.

Figure 7:
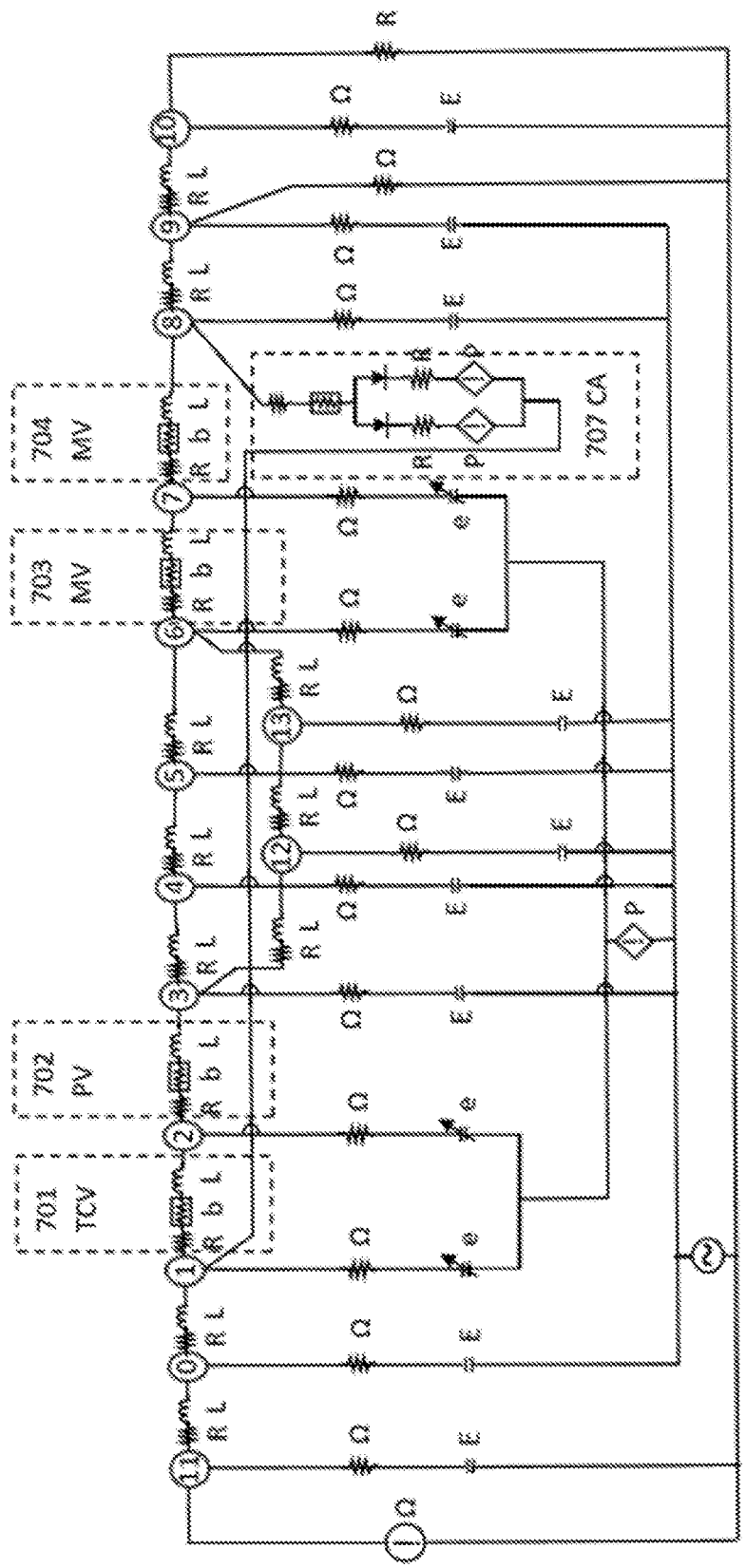
FIG. 7 shows a schematic representation of a lumped circuit, RLE model of a human cardio-vascular system of one embodiment of the present invention.

Making an accurate simulation of how a patient's cardio-vascular system would perform if the patient were to undergo a proposed surgical procedure may require an accurate mathematical model of the individual patent. In a preferred embodiment, the model used for the simulation may, for instance, be a sufficiently detailed lumped circuit mathematical model of the human cardio-vascular system, i.e., a full-system, closed loop model that may be representative of the cardio-vascular circulation of the entire body of a human. One embodiment of such a schematic representation of such a model is shown in FIG. 7, and is described in more detail below. Such a model typically relies on being loaded, or initialized, with appropriate values, or parameters, for each of the elements of the model. For the model to accurately simulate the behavior of a particular patient's cardio-vascular system, the model needs to be loaded with parameter's whose values are accurate for that specific, individual patient. As seen in FIG. 7, an adequate lumped parameter model may contain as many as 14 nodes, each of which may be joined by as many as four elements each representing, for instance, fluid flow, fluid pressure and fluid storage for various arteries and veins in the body. Each of these element may require at least one initial value, so that the model may need to be loaded with a hemodynamic calculation set that may contain hundreds of individual values. Databases exist of typical values of such hemodynamic calculation parameters. These databases are, for instance, based on experimental research data derived from measurements on various populations, as described in more detail in, for instance, U.S. Provisional Patent Application Ser. No. 62/523,445 filed Jun. 22, 2017 entitled "Global Multiscale Human Circulation Simulator", the contents of which are fully incorporated herein by reference In Step 201 "OBTAIN GENERIC HEMODYNAMIC CALCULATION PARAMETER SET", a generic set of such hemodynamic parameters may be obtained from one or more databases having typical values of such hemodynamic calculation parameters. This generic set of parameters may then be used to initially populate the mathematical hemodynamic model of the hemodynamic simulation module.

The generic hemodynamic calculation parameter set may, for instance, be derived from data representative of one or more populations having one or more observable characteristics in common with the patient. These observable characteristics may, for instance, be demographic features such as, but not limited to, age, gender, or ethnicity; or measurable observables such as, but not limited to, weight, or height; or historical attributes such as, but not limited to, diet, or a history regarding prior surgeries, alcohol consumption, smoking, drug use, medication use, or some combination thereof.

In Step 202 "ADJUST GENERIC HEMODYNAMIC CALCULATION PARAMETER SET", the generic hemodynamic calculation parameter set may be adjusted to more accurately reflect the detailed working of an individual patients cardio-vascular system. The adjustment may be necessary because, while the generic parameter set may be chosen from data representative of a population, or sub-population, having observable characteristics in common with the individual patient, they still may not accurately reflect the individual patient.

This adjustment may be accomplished by, for instance, first obtaining a measured, hemodynamic profile of the patient in a first situation, such as, but not limited to, when the patient is seated in a temperature controlled room. By then comparing how accurately the hemodynamic simulation module is able to simulate that hemodynamic profile, the generic hemodynamic calculation parameter set may be adjusted until a required degree of accuracy may be obtained. This adjustment may be performed by a skilled clinician, or it may be performed automatically using mathematical, optimization routines, or it may be done by a combination of the two. For additional accuracy, more than one measured situation may be used. The patient may, for instance, be measured while in two or more situations such as, but not limited to, when standing or when lying prone, or during or after a specific exercise routine such as, but not limited to, walking on a treadmill for a given time at a given rate, or to obtain a given result such as, but not limited to, elevating a pulse rate by a certain percentage or to a given rate, or some combination thereof.

Step 203 "RESULT IN PATIENT SPECIFIC HEMODYNAMIC CALCULATION PARAMETER SET" shows the end result of the adjustments made in the previous step, namely a patient specific hemodynamic calculation parameter set. This may be the data necessary to initialize the hemodynamic simulation module so that accurate simulations may be made of the cardio-vascular response of the individual patient in any situation such as, but not limited to, a surgical situation.

Figure 3:
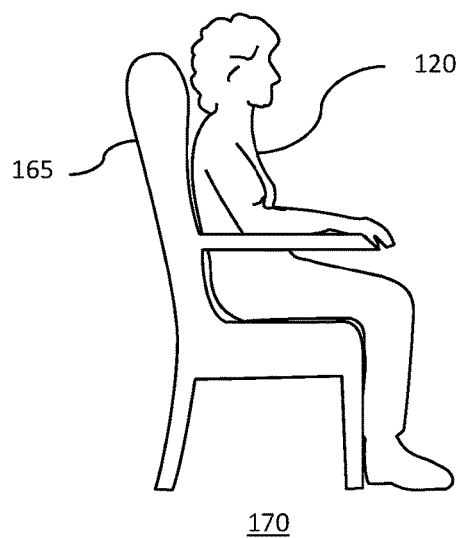
FIG. 3 shows a schematic representation of a patient in a first situation.

FIG. 3 shows a schematic representation of a patient in a first situation 170.

As depicted in FIG. 3, the first situation may involve the patient 120 being seated in a chair 165, while being in a temperature controlled room. This may be a situation in which the patient may be comfortable, and which may also be suitable for making the measurements necessary to obtain a measured, first situation, hemodynamic profile of the patient.

The measured, first situation, hemodynamic profile may, for instance, include measured parameters such as, but not limited to, a systolic and a diastolic arterial blood pressures; one or more cardiac parameters such as, but not limited to, a heart rate, a systolic and a diastolic, right and left, ventricular pressure; and one or more respiration parameters, such as, but not limited to, an arterial and a venous oxygen saturation; or some combination thereof.

The measured, hemodynamic profile obtained in this first situation may then be used in the adjustment, or optimization of the hemodynamic simulation module so that it may be used to accurately simulate the patient's cardio-vascular performance in other situations, such as, but not limited to, situations necessary for undergoing various surgical procedures.

Although only one situation is shown, increased accuracy may be obtained by, for instance, obtaining measurements of the patient in multiple situations that may, for instance, include situations in which the patient has been stressed to a known degree by, for instance, exercise sufficient to produce a predetermined alteration in, for instance, a patient's pulse rate.

Figure 4:
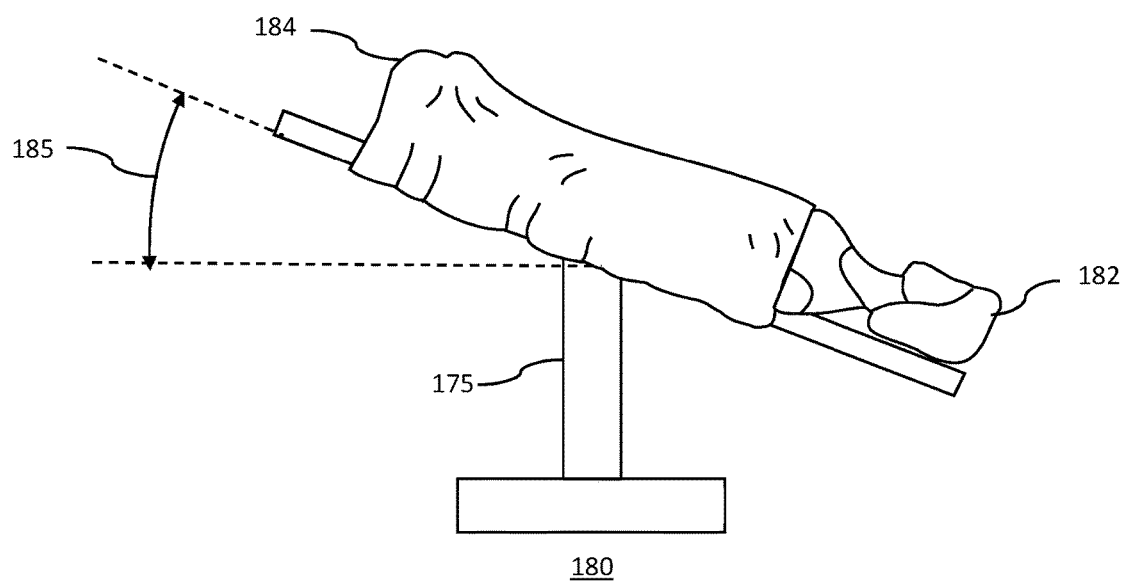
FIG. 4 shows a schematic representation of a patient in an operating situation.

FIG. 4 shows a schematic representation of a patient in an operating situation 180.

As shown in FIG. 4, the patient is shown situated on a tilting operating table 175 such that the patient's head 182 is significantly lower than the patient's feet 184. This may, for instance, be the Trendelenburg, position, or head down position. Although originally used to care for patients in shock, it, and related tilted positions, are now typically used surgeries such as, but not limited to, laparoscopic surgery where it may afford the surgeon better access to, and visibility of, portions of the body being operated on. In the classic Trendelenburg position, the angle of tilt of the patient 185 may be between 15 to 30 degrees. More recently, operations have been conducted in which the angle of tilt of the patient may be greater, with the patient's feet 184 being elevated by as much as 60 degrees above the patient's head 182. There are also operations that are now typically performed with a reverse Trendelenburg position, i.e., with the patient's head raised above the patient's feet. This may, for instance, be useful when surgery may being performed on organs situated below the stomach.

In laparoscopic surgery, the patient's abdominal cavity may also be insufflated, typically with carbon dioxide, also to provide better access and visibility.

These conditions, the tilt and the insufflation, may have adverse hemodynamic effects such as, but not limited to, increased blood pressure and reduced cardiac output. It may, therefore, be important to ensure that a patient is in sufficiently good health to endure these adverse effects before subjecting the patient to the procedure. This may, for instance, be accomplished by simulating, the hemodynamic consequences of placing a particular patient in such a surgical situation before actually performing the surgery. Because some complex surgeries require a significant amount of time, often 4-hours or more, it may be useful to simulate the hemodynamic profile over a comparable period of time. For convenience, this may require performing the calculations using a digital processor, and a suitably configured hemodynamic model, such that the simulation may be performed in hyper-real time. For instance, it would be useful to simulate the effects of a 4-hour procedure in 1-hour or less. A requirement may, for instance, be the ability to simulate one hour in one minute.

Figure 5:
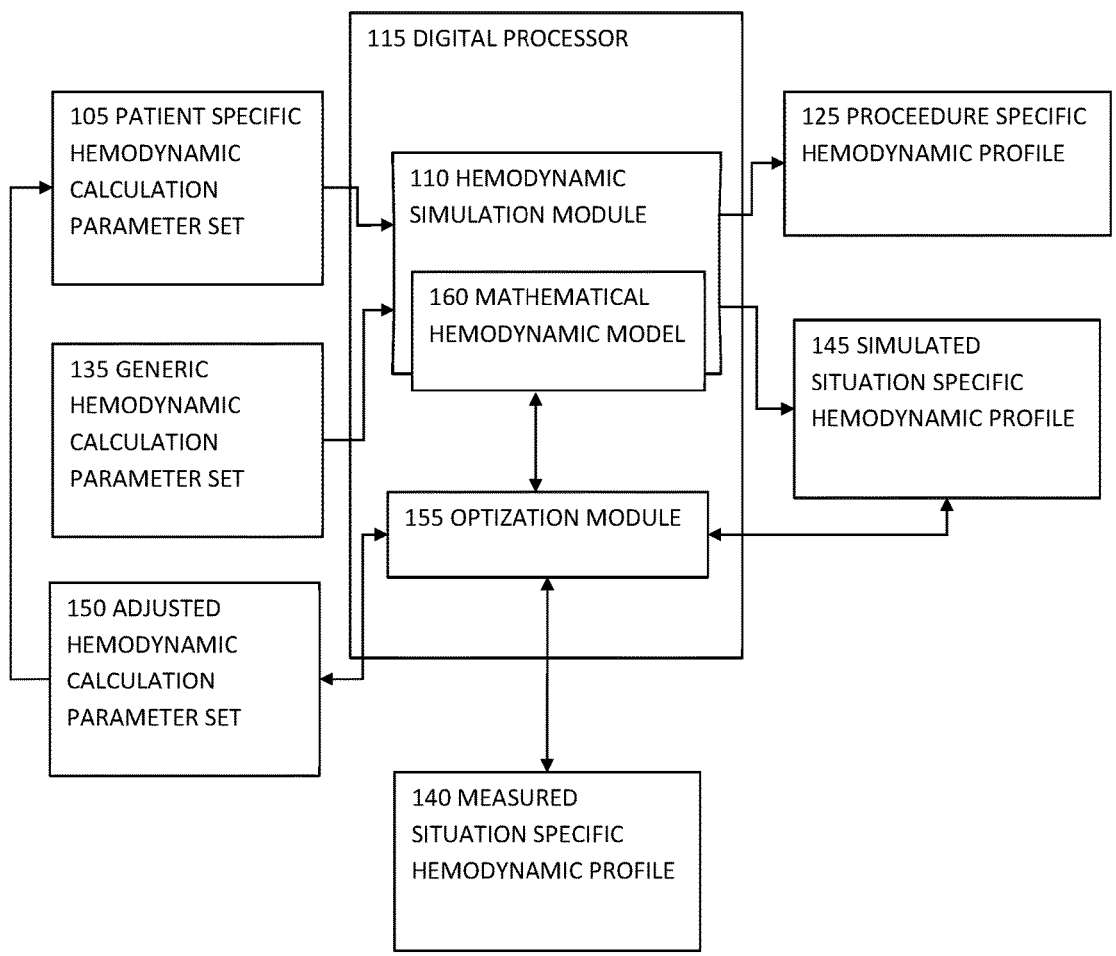
FIG. 5 shows a schematic representation of a system for determining a patient's suitability for a proposed surgical procedure of one embodiment of the present invention.

FIG. 5 shows a schematic representation of a system for determining a patient's suitability for a proposed surgical procedure of one embodiment of the present invention.

A digital processor 115 is shown hosting two computational software modules, a hemodynamic simulation module 110 and an optimization module 155.

The hemodynamic simulation module 110 may incorporate a mathematical hemodynamic model 160 that may, for instance, be a lumped circuit, model that mathematically models the human cardio-vascular system, as described in more detail in, for instance, U.S. Provisional Patent Application Ser. No. 62/523,445 filed Jun. 22, 2017 entitled "Global Multiscale Human Circulation Simulator", the contents of which are fully incorporated herein by reference. The model is preferably a full-system, closed loop, model, representative of the cardio-vascular circulation of the entire body of a human.

A function of the hemodynamic simulation module 110 may be to use a patient specific hemodynamic calculation parameter set 105 in order to calculate a simulated, procedure specific, hemodynamic profile 125 of the patient. This simulated, procedure specific, hemodynamic profile 125 may, for instance, be data indicative of how a specific patient's cardio-vascular system may respond to the patient being in a particular situation such as, but not limited to, a laparoscopic surgical procedure in which the patient may be required to be in a heads down orientation while having their abdominal cavity suffused with carbon dioxide over many hours.

In order to ensure that the output data is sufficiently accurate for a trained clinician to make a reliable judgement as to a patient's suitability for a particular surgery, the patient specific hemodynamic calculation parameter set 105 is preferably as representative of the individual patient as is reasonably possible. This may be accomplished using mathematical techniques used in an analogous problem, the optimization of optical lenses.

In the analogous art of lens design, an initial solution made up of a number of lenses in an initial configuration may be proposed, along with a required performance of the lens, typically expressed as a required value of a merit function. The merit function is typically made up of a weighted collection of measurable performance characteristics, typically the allowed size of various optical aberrations such as depth of focus, chromatic aberration and astigmatism, or some combination thereof. The performance of the proposed lens design may then be calculated. If the performance is not adequate, the construction parameters of the design may then varied. These construction parameters are typically the radii of the lenses, the glass the lenses are made of, etc. This may be repeated until a satisfactory solution is found.

There are well-known mathematical procedures for varying the design, or construction, parameters to most efficiently arrive at the parameters that produce the required lens performance. These methods are typically based on the Damped Least Squares method, which is a modification of the Gauss-Newton method. These and related methods of optimization are described in more detail, in, for instance, "Comparison of the classical dumped least squares and genetic algorithm in the optimization of the doublet" published by Vasiljevic et al. in the Proceedings of the First Workshop on soft computing, in Nagoya, Japan, August, pp. 200-204, the contents of which are fully incorporated herein by reference.

In a preferred embodiment of the present invention, an analogous process may be used in the optimization module 155 to optimize, or adjust, a generic hemodynamic calculation parameter set 135 to produce the required patient specific hemodynamic calculation parameter set 105. This may be done in an iterative process in which the hemodynamic simulation module 110 may use a generic hemodynamic calculation parameter set 135 to initially calculate a simulated, first situation, hemodynamic profile 145. The first situation may be one in which measurements may be made on the patient, such as, but not limited to, having the patient seated at room temperature, i.e., 20 degrees Celsius, in a temperature controlled environment. Other measurable, first situations may, for instance, be having the patient in a position such as, but not limited to, standing, or lying prone, either face up or face down. A measured, first situation, hemodynamic profile 140 of the patient may then be obtained, i.e., measurements made of one or more hemodynamic parameters of the patient in the specific, first situation. These hemodynamic parameters may, for instance, include measurable parameters such as, but not limited to, a systolic and a diastolic arterial blood pressures; one or more cardiac parameters such as, but not limited to, a heart rate, a systolic and a diastolic, right and left, ventricular pressure; and one or more respiration parameters, such as, but not limited to, an arterial and a venous oxygen saturation; or some combination thereof.

The optimization module 155 may then be used to compare the simulated results with the measured results. Adjustments may then be made to the generic hemodynamic calculation parameter set 135 to produce an adjusted, hemodynamic calculation parameter set 150 intended to make the simulated results more closely match the measured results. These adjustments may be made using the mathematical techniques of optimization, such as, but not limited to, the Damped Least Squares method, or they may be made by a skilled clinician, or they may be made by a combination of the two. These adjustments may continue in an iterative process of using the adjusted, hemodynamic calculation parameter set 150 to make a further simulated, first situation, hemodynamic profile 145 that may then be compared to the measured, first situation, hemodynamic profile 140. The iterations may continue until the simulated results agree with the measured results to a sufficient, or required, degree of accuracy, such as, but not limited to, being within a certain percentage of each other, such as all results agreeing to within 1%.

Once the simulated and measured results are in adequate agreement, the adjusted, hemodynamic calculation parameter set 150 may be designated a three patient specific hemodynamic calculation parameter set 105 and used to simulate simulated, procedure specific, hemodynamic profiles 125 of the patient in other situations, such as, but not limited to, surgical situations.

Figure 6:
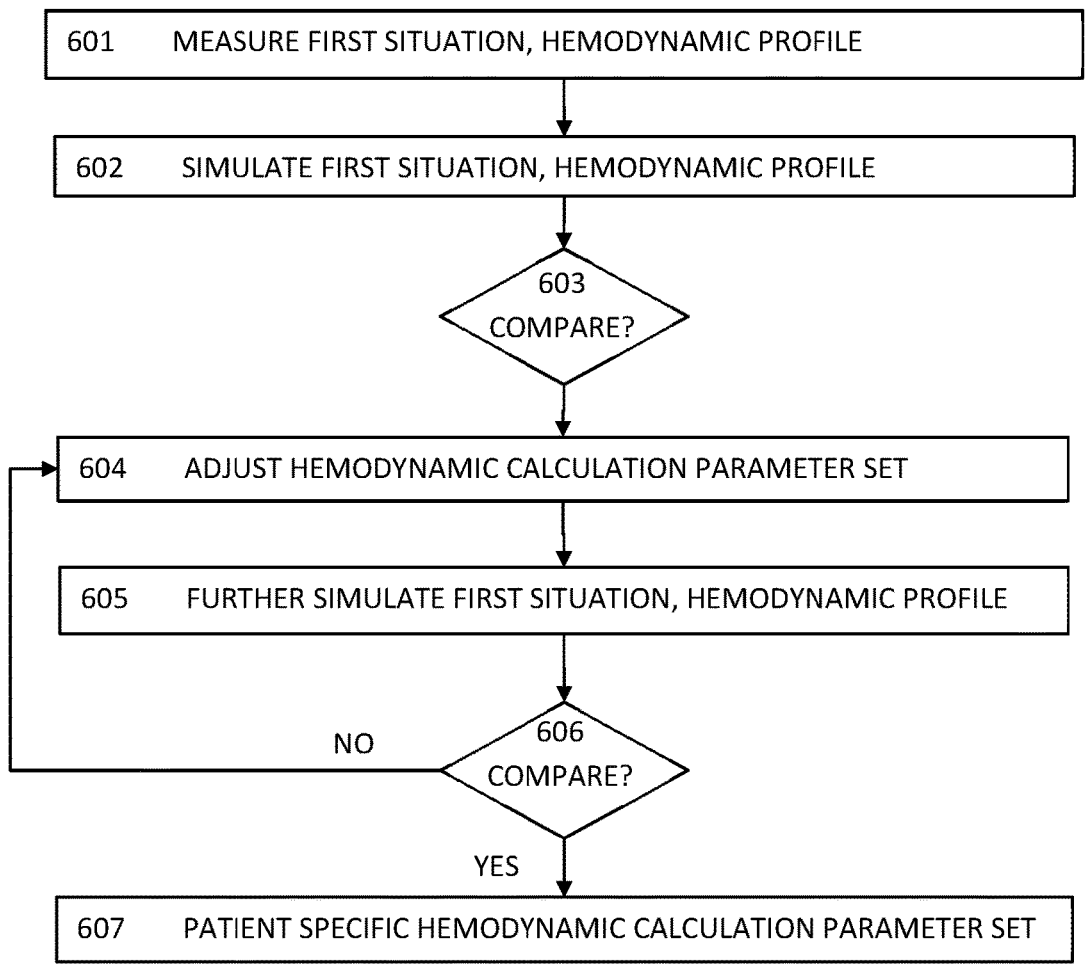
FIG. 6 is a schematic flow diagram showing representative steps for optimizing a generic hemodynamic calculation parameter set in order to produce a patient specific hemodynamic calculation parameter set of one embodiment of the present invention.

FIG. 6 is a schematic flow diagram showing representative steps for optimizing a generic hemodynamic calculation parameter set in order to produce a patient specific hemodynamic calculation parameter set of one embodiment of the present invention.

In Step 601 "MEASURE FIRST SITUATION, HEMODYNAMIC PROFILE", a hemodynamic profile of a patient may be measured. This may, for instance, consist of measuring one or more, measurable cardio-vascular related parameters of a patient while they are situated in a controlled environment. The measurable cardio-vascular related parameters may consist of data such as, but not limited to, a systolic and a diastolic arterial blood pressures; one or more cardiac parameters such as, but not limited to, a heart rate, a systolic and a diastolic, right and left, ventricular pressure; and one or more respiration parameters, such as, but not limited to, an arterial and a venous oxygen saturation; or some combination thereof.

The controlled environment may, for instance, be having the patient be seated and in a temperature controlled room. Other controlled environments may, for instance, be having the patient standing or lying prone, or having the patient perform exercise that may result in a predetermined change in a measurable parameter such as, but not limited to, their heart rate.

In Step 602 "SIMULATE FIRST SITUATION, HEMODYNAMIC PROFILE", a hemodynamic simulation module may be used to calculate a simulated, first situation, hemodynamic profile of the patient. This simulation may attempt to replicate the results of the measurements made in Step 601, and may contain one or more of the same cardiac parameters that were measured. The simulation may be performed using a generic hemodynamic calculation parameter set, selected to be representative of the patient, but which may not model the patient to the degree of precession required.

In Step 603 "COMPARE?" the measurement results obtained in Step 601 may be compared with the simulated results obtained in Step 602. This comparison may be on a parameter by parameter basis, or a target merit function may be used. The target merit function may be a measure of the overall performance of the patients cardio-vascular system, and may, for instance, include a sum of weighted, measurable hemodynamic parameters, and the comparison may be to see if that same merit function, populated with the simulated values, falls within an acceptable value when compared to the target value of the merit function.

If the comparison between measured and simulated results reveals too great a discrepancy, the optimization procedure may move to Step 604 "ADJUST HEMODYNAMIC CALCULATION PARAMETER SET". In this step, the calculation parameter set used in the mathematical hemodynamic model of the hemodynamic simulation module may be adjusted with the intention of improving the match between measured and simulated first situation hemodynamic values, or parameters. This adjustment may be performed by a suitably knowledgeable clinician, or it may be performed automatically by an optimization module, or it may require a combination of the two methods. When performed automatically, the process may proceed in a fashion that may be analogous to one or more of the optimization techniques used in optical lens design. The optimization module may, for instance, make use of a technique such as, but not limited to, to the Damped Least Squares method, to efficiently arrive at a solution for a merit function that may be both a local minimum value and satisfy the target value of the merit function. This may, however, be an iterative process in which, in Step 605 "FURTHER SIMULATE FIRST SITUATION, HEMODYNAMIC PROFILE", the hemodynamic simulation module may once again be used to produce a simulated, first situation, hemodynamic profile, but now using the adjusted, hemodynamic calculation parameter set. After that, in Step 606 "COMPARE?", the new simulated hemodynamic results may be compared with the measured hemodynamic results. If the comparison is still not satisfactory, the process may iterate back to Step 604, and further adjustments to the calculation parameter set may be made.

If, however, the simulated and measured results are in sufficient agreement, the current adjusted, hemodynamic calculation parameter set may be determined to be a sufficiently accurate patient specific hemodynamic calculation parameter set.

FIG. 7 shows a schematic representation of a lumped circuit, RLE model of a human cardio-vascular system of one embodiment of the present invention.

Lumped parameter models are a well-known mathematical method in fluid dynamics.

Using the analogies of, for instance, fluid flow to electrical current, fluid pressure to electrical voltage, and fluid storage to electrical capacitance, fluid systems may be described, and visualized, using the elements that are the same as, or similar to, standard electrical graphical elements used in drawing electronic circuits. Similarly, fluid flow may be mathematically analyzed using ordinary differential equations having forms analogous to those used in electronic engineering. Such systems and their application to hemodynamic models are described in more detail in, for instance U.S. Ser. No. 62/747,274 filed Oct. 18, 2018, entitled "Introduction to lumped hemodynamic models", the contents of which are fully incorporated herein by reference. The model shown in FIG. 7 is a 14-node RLE circuit, full-system, closed loop, model, representative of the cardio-vascular circulation of the entire body of a human, in which the following symbols are intended to have the following meaning:

R: Flow Resistance: represents the resistance encountered by flow due to the viscous behavior of the blood;

b: Quadratic resistance;

C: Vessel Compliance or Capacitance: represents the volume that accumulates in vascular regions as a consequence of an increase in pressure;

E: Vessel Elastance: represents the volume that accumulates in vascular regions taking due regard for the elastance of the vessel;

e: Time varying elastance.

Ω: Viscoelastance: represents a non-linear resistance to flow due to elastance of the vessel though which the flow occurs;

L: Fluid Inertance: represents an inertia in the blood flow during systolic acceleration and diastolic deceleration; and, P: Pressure.

As shown in FIG. 7, a satisfactory mathematical model of the human cardio-vascular system may be developed using the following 14 nodes that represent, Node 0: Vena Cava; Node 1: Right atrium, Node 2: Right ventricle; Node 3: Pulmonary arteries; Node 4: Pulmonary capillaries; Node 5: Pulmonary veins; Node 6: Left atrium; Node 7: Left ventricle; Node 8: Ascending Aorta; Node 9: Descending Aorta; Node 10: Peripheral arteries; Node 11: Systemic veins; Node 12: Pulmonary capillary wedge; and Node 13: Pulmonary capillary venous.

A cycle of the human cardio-vascular system may be simulated beginning at Node 11: representing the systemic veins (node 11), which are a set of veins that carry deoxygenated blood from various parts of the body back towards the heart. The blood may be collected in the vena cava (node 0), a vessel that collects the deoxygenated blood from varies of the systemic veins. From the vena cava the blood may enter the right atrium (node 1) of the heart. From there the flow circulates through the heart's tricuspid valve 701 to the right ventricle (node 2). From the right ventricle, blood may be pumped through the pulmonary valve 702 into the pulmonary region. In the pulmonary region, blood may pass through the pulmonary arteries (node 3) to the pulmonary capillaries (node 4), where it may be oxygenated. The oxygenated blood may then flow back to the heart via the pulmonary veins (node 5) into the left atrium (node 6). From the left atrium, the oxygenated blood flows via the mitral valve 703 into the left ventricle (node 7). From the left ventricle, oxygenated blood may be pumped through the aortic valve 704 into the ascending aorta (node 8). From the aorta, the blood flow may fan out to feed the various parts of the body. The first junction may be the coronary artery 707, where blood flows into the heart tissues to oxygenate the heart muscles, and then back into the heart via the right atrium (node 1). Blood from the ascending aorta may then flow on through various parts of the body and back to the heart via the vena cava (node 0). In the model shown in FIG. 7, blood flows through the descending aorta (node 9) and the peripheral arteries (node 10) are distinguished, with some of the flow returning more directly to the vena cava, while other flows are routed back to the heart via the systemic veins (node 11) and then on to the vena cava.

In the model shown in FIG. 7, the branch from the left atrium (node 6) to the capillary wedge (node 12) and pulmonary capillary venous (node 13) back to the left atrium (node 6) are there to allow the simulation of a pulmonary wedge, a common diagnostic inserted into patient's during certain surgical procedures.

The lumped circuit model shown in FIG. 7 may be used to both adequately represent the human cardio-vascular circulation, yet be compact enough to be calculated rapidly by existing digital processors. It may, for instance, be used to calculate simulated, procedure specific, hemodynamic profiles of patients in real-time, or even in hyper-real-time. Hyper-real-time calculation may, for instance, be used to calculate the effects of long exposures to anticipated surgical situations. In this manner, a surgery lasting for four or more hours may be simulated in, for instance, under an hour.

Although this invention has been described with a certain degree of particularity, it is to be understood that the present disclosure has been made only by way of illustration and that numerous changes in the details of construction and arrangement of parts may be resorted to without departing from the spirit and the scope of the invention.

The invention claimed is:

1. A method for determining a patient's suitability for a proposed surgical procedure, comprising:
   producing a patient specific hemodynamic calculation parameter set using the optimizing method comprising:
      obtaining a generic hemodynamic calculation parameter set;

producing a measured, first situation, hemodynamic profile of said patient by measuring one or more hemodynamic parameters of said patient in a first situation;

producing a simulated, first situation, hemodynamic profile of said patient, using said generic hemodynamic calculation parameter set, and a hemodynamic simulation module;

comparing said measured, first situation, hemodynamic profile to said simulated, first situation, hemodynamic profile; and based on said comparison, adjusting said generic hemodynamic calculation parameter set to produce an adjusted, hemodynamic calculation parameter set;

producing a further simulated, first situation, hemodynamic profile of said patient, using said adjusted hemodynamic calculation parameter set and said hemodynamic simulation module;

comparing said measured, first situation, hemodynamic profile to said further simulated, first situation, hemodynamic profile; and repeating the previous three steps until a sufficiently good agreement is reached between said profiles, then designating the final adjusted hemodynamic calculation parameter set as the patient specific hemodynamic calculation parameter set;

using said patient specific hemodynamic calculation parameter set, and said hemodynamic simulation module, operable on a digital processor, to automatically produce a simulated, procedure specific, hemodynamic profile of said patient; and evaluating said simulated, procedure specific, hemodynamic profile to determine if said patient is a suitable candidate for said surgical procedure.

2. The method of claim 1 wherein, said generic hemodynamic calculation parameter set comprises data representative of a population having one or more observable characteristics in common with said patient.

3. The method of claim 2, wherein, said observable characteristics are one of an age, a gender, an ethnicity, a weight, a height, a diet, a history of prior surgery, a history of medication use, a history of alcohol consumption, a history of smoking, a history of drug use, or some combination thereof.

4. The method of, claim 1 wherein, said measured, first situation, hemodynamic profile comprises at least one of a systolic and a diastolic arterial blood pressures, a cardiac parameter comprising a heart rate, a systolic and a diastolic, right and left, ventricular pressure, and a respiration parameter, comprising an arterial and a venous oxygen saturation, or some combination thereof.

5. The method of claim 1 wherein said adjusting is performed automatically by an optimization module operative on said digital computer.

6. The method of claim 5, wherein, said optimization module utilizes an algorithm comprising a Damped Least Squares Method.

7. The method of, claim 1 wherein said comparing further comprises:
defining a merit function representative of said measured, first situation, hemodynamic profile of said patient; and
wherein, comparing comprises, comparing a value of said merit function obtained using said simulated, first situation, hemodynamic profile to a target value of said merit function.

8. The method of claim 7, wherein, said merit function comprises a weighted sum of two or more of said measured, first situation, hemodynamic parameters.

9. The method of claim 1, wherein, said hemodynamic simulation module comprises a full-system, closed loop, mathematical hemodynamic model representative of the cardio-vascular circulation of the entire body of a human.

10. The method of claim 9, wherein, said mathematical hemodynamic model comprises a lumped circuit model.

11. The method of claim 9, wherein, said lumped circuit model is a 14-node RLE circuit model.

* * * * *